(12) United States Patent
Bruder et al.

(10) Patent No.: US 11,104,624 B2
(45) Date of Patent: Aug. 31, 2021

(54) METHOD AND SYSTEM FOR PRODUCING BENZENE

(71) Applicant: LINDE AKTIENGESELLSCHAFT, Munich (DE)

(72) Inventors: David Bruder, Munich (DE); Torben Hofel, Munich (DE); Benedikt Kurz, Munich (DE); Karlheinz Brudi, Neubiberg (DE); Matthias Andre, Munich (DE); Anne Spindelndreher, Penzberg (DE); Richard Koller, Munich (DE); Heinz Zimmermann, Munich (DE)

(73) Assignee: LINDE AKTIENGESELLSCHAFT, Munich (DE)

( * ) Notice: Subject to any disclaimer, the term of this patent is extended or adjusted under 35 U.S.C. 154(b) by 44 days.

(21) Appl. No.: 16/331,815

(22) PCT Filed: Sep. 8, 2017

(86) PCT No.: PCT/EP2017/072600
§ 371 (c)(1),
(2) Date: Mar. 8, 2019

(87) PCT Pub. No.: WO2018/046671
PCT Pub. Date: Mar. 15, 2018

(65) Prior Publication Data
US 2019/0367430 A1    Dec. 5, 2019

(30) Foreign Application Priority Data
Sep. 8, 2016   (EP) .................................. 16187895

(51) Int. Cl.
*C07C 4/16*   (2006.01)
*C07C 4/20*   (2006.01)

(52) U.S. Cl.
CPC . *C07C 4/16* (2013.01); *C07C 4/20* (2013.01)

(58) Field of Classification Search
None
See application file for complete search history.

(56) References Cited

U.S. PATENT DOCUMENTS 3,322,842 A * 5/1967 Czajkowski .............. C07C 4/18
585/488
4,167,533 A * 9/1979 Raymond ............... C07C 15/04
208/67

(Continued)

FOREIGN PATENT DOCUMENTS

DE      2814367 A1    10/1978

*Primary Examiner* — Philip Y Louie
(74) *Attorney, Agent, or Firm* — Fay Sharpe LLP

(57) ABSTRACT

A method (100) is proposed for the manufacture of benzene, in which a first feedstock mixture is formed, which contains alkylated aromatics and hydrogen, and in which the alkylated aromatics contained in the first feedstock mixture are partially converted with the hydrogen contained in the first feedstock mixture to the benzene through hydrodealkylation (33), thereby obtaining a first product mixture, wherein the first product mixture contains the benzene, the unconverted alkylated aromatics, alkanes with one to three carbon atoms formed in the conversion of the alkylated aromatics to the benzene, and the unconverted hydrogen, and wherein at least a part of the alkanes with one to three carbon atoms and of the hydrogen are separated from the first product mixture, thereby obtaining a light-gas fraction. It is proposed that the hydrogen contained in the first feedstock mixture is provided at least in part with the use of a low-temperature separation (18), to which at least a part of a second product mixture is supplied, wherein the second product mixture is formed at least in part through steam cracking (11) of a second feedstock mixture, and that the light-gas fraction is also supplied at least in part to the low-temperature separation (Continued)

(18). A corresponding plant also forms the subject matter of the invention.

12 Claims, 1 Drawing Sheet

(56) References Cited

U.S. PATENT DOCUMENTS

| | | | |
|---|---|---|---|
| 4,191,632 A | 3/1980 | Cosyns et al. | |
| 4,215,231 A * | 7/1980 | Raymond | C07C 4/16 208/67 |
| 2013/0174604 A1 * | 7/2013 | Peschel | F25J 3/0635 62/618 |
| 2014/0171704 A1 * | 6/2014 | Erisken | C10G 11/00 585/303 |

* cited by examiner

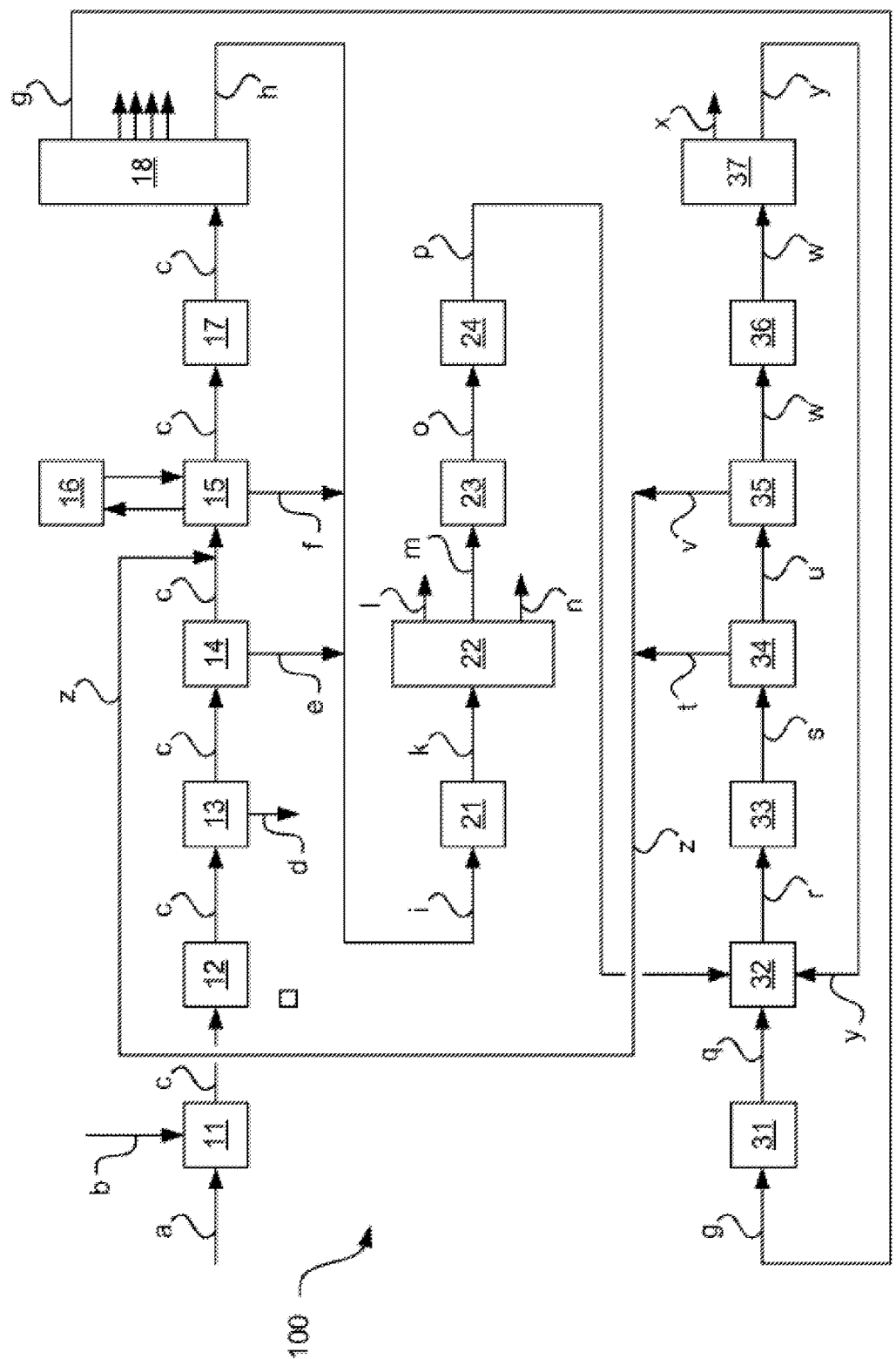

METHOD AND SYSTEM FOR PRODUCING BENZENE

The invention relates to a method and a plant for the manufacture of benzene according to the preambles of the independent claims.

PRIOR ART

Benzene can be manufactured through hydrodealkylation of compounds such as toluene, xylene and alkylated aromatics with nine carbon atoms. The named starting compounds are frequently obtained in the form of a so-called BTX fraction, which can be formed, for example, with the use of so-called pyrolysis gasoline, which occurs during steam cracking. Alternative sources are the reformate from catalytic reforming and the hydration gasoline from the carbonisation of coal.

Pyrolysis gasoline from steam cracking typically comprises predominantly or exclusively hydrocarbons with 5 to 10 carbon atoms, of which predominantly aromatics. The aliphatics contained are predominantly unsaturated and comprise a high proportion of acetylene and dienes. The pyrolysis gasoline is accordingly unstable and cannot be stored because of the tendency towards polymerisation of the named components. It is therefore further treated in several steps. For example, a selective hydration can initially take place in order to convert acetylenes, dienes and styrenes to olefins. After the separation of higher molecular components, the correspondingly treated pyrolysis gasoline can then be supplied for a separation, in which typically, inter alia, a fraction is formed, which contains predominantly or exclusively hydrocarbons with 6 to 8 carbon atoms. This is the so-called "heart cut" (English: Heart Cut).

The heart cut can be subjected to a hydro-desulphurisation, in which olefins are converted to paraffins and naphthenes, and organically bound sulphur is converted to hydrogen sulphide, which can be removed in a downstream stripper. The correspondingly treated heart cut can then be subjected to an aromatic extraction, in which the BTX fraction is separated from the aliphatics.

In the case of the hydrodealkylation, alkyl residues are stripped from the benzene ring, generally with the use of one hydrogen molecule in each case and with the formation of the corresponding alkanes. Catalytic and thermal hydrodealkylation methods are known. These methods have in common the fact that in each case hydrogen must be supplied for the hydrodealkylation.

In order to supply hydrogen for large-scale technical processes, reforming methods, for example, catalytic reforming in refineries or steam reforming, are typically used. In the latter case, hydrocarbons are supplied with steam to one or more catalytic reactors and converted there, inter alia, into carbon monoxide and hydrogen, that is, into synthesis gas. In order to increase the hydrogen content, a hydrogen-gas shift is then typically used, in which carbon monoxide is converted with water into further hydrogen and carbon dioxide. The hydrogen can then be separated.

For details of hydrodealkylation and hydrogen recovery, reference is made to the relevant specialist literature, for example, the article "benzene" in Ullmann's Encyclopedia of Industrial Chemistry, online since 15 Jun. 2000, DOI 10.1002/14356007.a03_475, especially section 5.3.1, "Hydrodealkylation", and the article "Hydrogen" in Ullmann's Encyclopedia of Industrial Chemistry, online edition 15th June 2000, DOI: 10.1002/14356007.a13_297.

In the recovery of hydrogen from synthesis gas for use in the hydrodealkylation, a low-temperature separation is typically used, which is disposed upstream of the hydro-desulphurisation. Furthermore, in the hydro-desulphurisation of unconverted hydrogen which is to be re-used in the hydro-desulphurisation, traces of benzene must be removed, traditionally in an effort-intensive manner. Since sulphur compounds are typically added in the case of the hydrodealkylation in order to prevent the coking of the reactors, a final alkali wash is required. Alongside this, a benzene absorber column is used in the hydrodealkylations, which has the object of minimising benzene losses in the light-gas flow.

The named factors increase costs and the demand on apparatus in the manufacture of benzene through hydrodealkylation. The object of the present invention is to achieve improvements in this context.

DISCLOSURE OF THE INVENTION

Against this background, the present invention proposes a method and a plant for the manufacture of benzene with the features of the independent claims. In each case, further developments form the subject matter of the dependent claims and the subsequent description.

Before explaining the features and advantages of the present invention, their basic principles and the terminology used will be explained.

In the conventional usage here, liquid and gaseous mixtures can be rich or poor in one or more components, wherein "rich" can stand for a content of at least 50%, 75%, 90%, 95%, 99%, 99.5%, 99.9% or 99.99%, and "poor" can stand for a maximum content of 50%, 25%, 10%, 5%, 1%, 0.1% or 0.01% on a molar, weight or volume basis. The term "predominantly" can correspond to the definition of "rich". In the linguistic convention used here, liquid and gaseous mixtures can, furthermore, be enriched or depleted in one or more components, wherein these terms relate to a corresponding content in a starting mixture from which the liquid or gaseous stream was obtained. The liquid or gaseous mixture is "enriched" when it contains at least the 1.1-fold, 1.5-fold, 2-fold, 5-fold, 10-fold, 100-fold or 1000-fold content; it is "depleted" when it contains at most the 0.9-fold, 0.5-fold, 0.1-fold, 0.01-fold or 0.001-fold content of a corresponding component, with reference to the starting mixture. In the present case, for example, when reference is made to "methane" or "hydrogen" or respectively a corresponding fraction, what should also be understood by this is also a mixture which is rich in the corresponding component. However, this may also refer to the respective pure gas.

A liquid or gaseous mixture is "derived" from another liquid or gaseous mixture (also designated as a starting mixture) or "formed" from this mixture or with the use of this mixture, if it comprises at least some of the components contained in the starting flow or obtained from this. A mixture formed in this sense can be formed from the starting mixture through separation or branching of a sub-flow or of one or more components, enrichment or depletion with reference to one or more components, chemical or physical conversion of one or more components, heating, cooling, compression and similar. However, a "formation", for example, of a feedstock mixture for a subsequent separation process, can also represent simply the guiding of a corresponding mixture in an appropriate pipeline and a supply into the separation process.

Advantages of the Invention

The present invention is based on the knowledge that an extensive integration of a hydrodealkylation and of a steam cracking method brings special advantages and at least partially overcomes the disadvantages mentioned in the introduction. Methods and corresponding plants for the recovery of olefins such as ethylene through steam cracking (English: Steam Cracking) are known and described, for example, in the article "Ethylene" in Ullmann's Encyclopedia of Industrial Chemistry, online since 15 Apr. 2009, DOI 10.1002/14356007.a10_045.pub3.

As is known, in the case of steam cracking, substance mixtures are formed which can be subjected to an appropriate conditioning and to known separation sequences for separation into components or component groups. One example for such a separation sequence is explained in greater detail with reference to the attached the FIGURE. Corresponding separation sequences are known from the cited prior art and differ substantially through the sequence of the separation steps used.

Typically, a corresponding substance mixture, also referred to in the following as a "product mixture" of the steam cracking, although such a substance mixture can contain not only the desired products but also by-products and unconverted educts, is initially subjected to a cooling, for example, in a linear cooler (English Transfer Line Exchanger, TLE). Following this, a separation of heavier components is implemented, typically with the use of an oil circulation and a water circulation. In this context, a pyrolysis gasoline fraction can be formed, and water can be recovered. Further pyrolysis gasoline is separated from the product mixture in a downstream compression. During the course of the compression, that is, especially in an intermediate stage of a utilised multi-stage compressor, an acidic gas removal is typically performed, typically with the use of an amine and/or alkali wash. The correspondingly conditioned product mixture is then dried and pre-cooled before it is subjected to a low-temperature separation.

The low-temperature separation can be constituted in the form of a so-called "de-ethaniser first", a "de-methaniser first" or a "de-propaniser first" method. For corresponding details, reference is made to the prior art cited above. In a corresponding low-temperature separation, a hydrogen fraction and a methane fraction are typically separated. The hydrogen fraction typically comprises a hydrogen content of 80%-95%. For the formation of a corresponding hydrogen fraction, a fraction containing, for example, predominantly or exclusively hydrogen and methane can also initially be formed, from which the hydrogen can then be separated, for example, with the use of a pressure-exchange adsorption. The hydrogen fraction is typically formed with the use of a known de-methaniser, in which heavier components are separated as liquid from a corresponding gas mixture.

Other fractions which can be formed in a corresponding low-temperature separation are, for example, a fraction which contains predominantly or exclusively hydrocarbons with two carbon atoms, especially ethane and ethylene. Ethylene fraction can be separated from this and supplied as a product. The ethane can be recycled, for example, for steam cracking. With regard to the recovery of other fractions, reference is made to the prior art. The corresponding low-temperature separation or respectively individual steps of the latter can be disposed especially upstream, between or downstream of hydration. The latter serves, in particular, to convert acetylene contained in the product mixture into the corresponding olefins. Especially, in a corresponding low-temperature separation, a further pyrolysis gasoline fraction can also be formed.

The present invention now proposes using the hydrogen fraction from the low-temperature separation of the steam cracking instead of a separately provided hydrogen fraction in the hydrodealkylation. In this manner, it is possible to dispense with the provision of a separate reforming method and the corresponding low-temperature separation steps and the absorber column. The hydrogen fraction from the low-temperature separation of the steam-cracking method proves sufficiently pure and is present in an appropriate condition to be used directly in the hydrodealkylation. By preference, only a compression of this hydrogen fraction is required in order to supply it to a corresponding reactor.

A further aspect of the present invention is the treatment of the hydrogen not converted in the hydrodealkylation, or respectively of a corresponding light-gas fraction. Such hydrogen is separated together with the short-chain alkanes formed in the dealkylation from a product mixture of the hydrodealkylation, forming a corresponding light gas fraction which contains these components. The light gas fraktion thus comprises, besides hydrogen, also short chained alcanes, particularly methane, optionally ethane and/or ethylene, and further optionally propane and/or propylene.

Conventionally, corresponding hydrogen must be purified in an effort-intensive manner in order to be re-used in the hydrodealkylation. By contrast with this, the present invention now proposes to supply this fraction to the separation, to which the product mixture of the steam cracking method is also subjected. In particular in this context, a corresponding fraction is supplied upstream to a compression in a corresponding separation sequence. As mentioned, during the course of such a compression, an amine or alkali wash is also implemented, in which acid gases are washed from a corresponding gas mixture. More generally, a sour gas removal is performed in the course of the separation to which the product mixture of the steam cracking method is submitted. In this context, the light gas fraction is advantageously guided into the separation not only upstream of the compression but also upstream of the sour gas removal, e.g. of an amine or alkali wash. As mentioned, since sulphur compounds are also used in the hydrodealkylation, and since these can be transferred into a corresponding product mixture and therefore also into the light-gas fraction, in this way a washing out or, depending of the method used, a removal of sulphur compounds in a different way can also take place without the need for a separate alkali wash or another separate method for sour gas removal.

Overall, the present invention proposes a method for the manufacture of benzene, in which a first feedstock mixture is formed, which contains alkylated aromatics and hydrogen, and in which the alkylated aromatics contained in the first feedstock mixture and the hydrogen contained in the first feedstock mixture are partially converted to benzene through hydrodealkylation, thereby obtaining a first product mixture. The first product mixture contains the benzene, the unconverted alkylated aromatics, alkanes with one to three carbon atoms formed in the conversion of the alkylated aromatics to the benzene and the unconverted hydrogen. To this extent, as known from the prior art, at least a part of the alkanes with one to three carbon atoms and of the hydrogen are separated from the first product mixture thereby obtaining a light-gas fraction. The light-gas fraction contains especially hydrogen and the named short-chain alkanes, but can also contain traces of benzene.

As already explained in other words, the present invention now proposes that the hydrogen contained in the first feedstock mixture is provided at least in part with the use of a low-temperature separation, to which at least a part of a second product mixture is supplied, wherein the second product mixture is formed at least in part through steam cracking of a second feedstock mixture, and that the light-gas fraction is supplied, similarly at least in part, to the low-temperature separation. With the method according to the invention, synergetic effects between a steam cracking method and a hydrodealkylation are exploited, which, in particular, allow a separate preparation of hydrogen for the hydrodealkylation and a separate treatment of a corresponding light-gas fraction to be dispensed with. Details and advantages have already been explained.

As already mentioned, the second product mixture or its part supplied to the low-temperature separation and the light-gas fraction or its part supplied to the low-temperature separation is compressed and then subjected to the low-temperature separation. As mentioned, during the course of the compression, an acidic gas removal is implemented, which is also especially advantageous for the treatment of the light-gas fraction from the hydrodealkylation. An acidic-gas removal takes place "during the course of the compression", because it is implemented especially at an intermediate pressure, that is, after one or more first, and before one or more second compression stages or respectively compression steps. Within the scope of the present invention, the acidic-gas removal can especially comprise an alkali wash and/or amine wash.

In other words, therefore, a low-temperature separation can be part of a separation sequence or processing sequence, wherein in this separation sequence or processing sequence, a compression and, in particular, a sour gas removal are carried out before the low-temperature separation. The sour gas removal does not have to take place in the course of the compression, as it was explained before. In any case, a synergy can be achieved in a particularly advantageous way by feeding the light gas fraction upstream of the compression and/or sour gas removal to the separation sequence or processing sequence. In this way, a separate sour gas removal can be dispensed with.

In principle, the hydrogen can be separated in an arbitrary manner in the low-temperature separation. However, it is advantageous if the low-temperature separation comprises a demethanisation, and if the hydrogen contained in the first feedstock mixture is provided at least in part with the use of the demethanisation. A corresponding method can take place as a first ("de-methaniser first"), second ("de-ethaniser first") or also as a further step in a corresponding separation sequence.

Furthermore, it is particularly advantageous if a pyrolysis gasoline fraction is provided with the use of at least a part of the second product mixture, that is, of the product mixture of the steam cracking method. As mentioned, a corresponding pyrolysis gasoline fraction can occur especially in a water wash, to which a corresponding product mixture is subjected. Further pyrolysis gasoline can be formed in the compression and in the low-temperature separation. The present invention now proposes the use of a corresponding pyrolysis gasoline fraction also for the recovery of benzene.

In this context, it is particularly advantageous if at least a part of the alkylated aromatics contained in the first feedstock mixture is provided through a conditioning of at least a part of the pyrolysis gasoline fraction. In this manner, a further substance integration can be achieved between the steam-cracking method and the hydrodealkylation.

It is accordingly particularly advantageous if the conditioning of the pyrolysis gasoline fraction or its part comprises a hydration and/or separation and/or hydro-desulphurisation and/or aromatic extraction. Corresponding steps will be selected by the person skilled in the art dependent upon requirements and also, especially dependent upon the composition of a corresponding pyrolysis gasoline fraction. For details, reference is made, for example, to the explanations for the FIGURE and also to the specialist literature. In particular, in the context of the present invention, for example, the first mixture can be formed in such a way that it is poor in or free of non-aromatic compounds in the sense described above. This can be achieved, for example, by forming the first feed mixture at least partially from one or more fractions of an aromatic extraction. In this way it can be prevented that significant amounts of compounds, which are known to increase the exothermicity of the hydrodealkylation in an excessive manner in their presence, enter the hydrodealkylation. In this way, the use of separate process steps is avoided.

As already mentioned, within the scope of the invention, a separate provision of hydrogen for the hydrodealkylation can be dispensed with. However, the hydrogen provided in the low-temperature separation and contained in the first feedstock mixture is advantageously subjected to a compression for the formation of the first feedstock mixture, so that this hydrogen is also present at a pressure appropriate for a hydrodealkylation.

In particular, the method of the present invention is suitable for steam-cracking methods, to which liquid feedstocks are subjected. The second feedstock mixture accordingly contains especially naphtha. The alkylated aromatics advantageously comprise toluene and xylenes.

Furthermore, downstream of the hydrodealkylation, at least a part of the benzene and of the unconverted alkylated aromatics are separated from the first product mixture, thereby obtaining a liquid fraction. With the use of at least a part of this liquid fraction, a fraction containing predominantly or exclusively benzene and a fraction containing predominantly or exclusively unconverted alkylated aromatics is then formed. The former can be output as a product fraction; the latter can especially be recycled, at least in part to the hydrodealkylation.

Furthermore, the present invention relates to a plant for the manufacture of benzene, with regard to which reference is made to the corresponding patent claim. A corresponding plant is especially equipped for the implementation of a method as explained previously and, for this purpose, comprises correspondingly equipped means. With regard to features and advantages of a corresponding plant, reference is therefore made to the above explanations regarding the method according to the invention and its embodiments.

In the following, the invention is explained in greater detail with reference to the attached drawing which shows a preferred embodiment of the method according to the invention.

BRIEF DESCRIPTION OF THE DRAWING

The FIGURE shows a method according to an embodiment of the invention in the form of a schematic flow diagram.

DETAILED DESCRIPTION OF THE DRAWING

The FIGURE shows a process according to a particularly preferred embodiment of the invention. The method as a whole is marked with 100. In the following, when method features or respectively method steps are explained, these explanations relate equally to elements provided in a corresponding plant. When the method is described in the following, the corresponding explanations apply in the same manner with regard to the corresponding plant.

In the method 100 shown in the FIGURE, a hydrocarbon flow a and a steam flow b are supplied to a steam-cracking furnace 11. In this context, a cracking gas is formed and output from the steam-cracking furnace 11 in the form of a cracking-gas flow c. The illustration here has been considerably simplified to the extent that in practice, several feedstock flows and/or steam flows and additionally recycled substance flows and similar can be used, which can be supplied to one or more steam-cracking furnaces, which can be operated under identical or different conditions. For example, one or more steam-cracking furnaces designed for (completely, predominantly or partially) liquid feedstock flows and/or one or more steam-cracking furnaces designed for (completely, predominantly or partially) gaseous feedstock flows can be provided. Accordingly, several cracking-gas flows can also be formed, which can, for example, be combined. The substance flows and plant components explained in the following can also be present singly or in multiples.

In the illustrated example, the cracking-gas flow c is supplied to a cooling 12, for example, with the use of a Transfer Line Exchanger. In a primary fractionation 13, heavy components with a boiling point of typically greater than 200° C. are separated from the cracking gas, for example, with the use of an oil circulation or by means of other methods known from the prior art, and removed, in the illustrated example, in the form of a pyrolysis oil flow d. The cracking gas, with heavy components accordingly removed, is supplied in the form of the cracking-gas flow now designated with c to a water wash 13, where components of the pyrolysis gasoline fraction are removed with the use of scrubbing water, and separated by condensation from the steam used in the cracking. These hydrocarbon components can also be recycled, for example, into the primary fractionation 13 and used there for washing out the heavy components. At least a part of the pyrolysis gasoline fraction is removed in the illustrated example in the form of a pyrolysis gasoline flow e.

In the illustrated example, even if a substance flow z (see below) is fed into the cracking-gas flow, a corresponding combined flow is still designated with c here. The latter is supplied to a compression 15, with which an acidic gas removal 16 is associated. The compression 15 takes place over several stages; in an intermediate stage, the compressed substance flow is guided to the acidic gas removal 16. Other configurations are also possible. In the compression, further components of the pyrolysis gasoline fraction are separated, which are removed in the form of a further pyrolysis gasoline flow f. The gas mixture with acidic gases removed is now supplied in the form of a substance flow still designated with c to a pre-cooling and drying 17, where residual water is removed, and pre-cooled before it is fed into a low-temperature separation 18. For details of the low-temperature separation 18, reference is made to the specialist literature cited in the introduction. The low-temperature separation 18 is shown in the form of a single unit merely for the purpose of visual clarity. In practice, sequentially arranged separation units (for example, de-ethanisers, de-methanisers, de-propanisers etc.) are provided in a corresponding low-temperature separation 18.

In the low-temperature separation 18, a series of fractions is formed from the cracking gas, of which, in the present case, only one hydrogen fraction and one further pyrolysis gasoline fraction are of interest and will therefore be explained in greater detail. These are output from the low-temperature separation 18 in the form of a hydrogen flow g and a further pyrolysis gasoline flow h. The hydrogen fraction can be separated, for example, from a gas mixture containing predominantly or exclusively hydrogen and methane, which is formed in the low-temperature separation in a de-methaniser. As mentioned, it contains, for example, 90% hydrogen. The pyrolysis gasoline fraction is formed, for example, in a de-butaniser, in which hydrocarbons with four carbon atoms are separated from a substance mixture containing these hydrocarbons with four carbon atoms and heavier hydrocarbons. The pyrolysis gasoline fraction formed in the de-butaniser accordingly contains the named heavier hydrocarbons, especially hydrocarbons with 5 to 10 carbon atoms.

Further fractions formed in the low-temperature separation 18, which are not explained separately here, comprise, for example, a fraction which contains predominantly or exclusively methane, a fraction which contains predominantly or exclusively hydrocarbons with two carbon atoms, a fraction which contains predominantly or exclusively hydrocarbons with three carbon atoms and a fraction which contains predominantly or exclusively hydrocarbons with two carbon atoms. Sub-fractions of corresponding fractions can also be formed, for example, from the fraction which contains predominantly or exclusively hydrocarbons with two carbon atoms, a fraction which contains predominantly or exclusively ethylene and a fraction which contains predominantly or exclusively ethane can be formed. The latter can be recycled, for example, into the cracking furnace 11 or one of several such cracking furnaces, especially a separate cracking furnace designed for gaseous feedstocks. The same also applies for the other fractions. All of the fractions can be subjected to appropriate post-treatment, separation, conversion and conditioning steps. The low-temperature separation 18 can also comprise, for example, hydration steps, or such hydration steps can be arranged upstream and/or downstream of the low-temperature separation 18.

The pyrolysis gasoline flows e, f and h within the scope of the embodiment of the invention illustrated here are combined in one pyrolysis gasoline combined flow i, but can also be used separately. The pyrolysis gasoline fraction from steam cracking comprises predominantly or exclusively hydrocarbons with 5 to 10 carbon atoms, of which predominantly aromatics. The aliphatics contained are predominantly unsaturated and comprise a high proportion of acetylene and dienes. The pyrolysis gasoline fraction is accordingly unstable and cannot be stored because of the tendency towards polymerisation of the named components. Dependent upon the method steps arranged downstream, the pyrolysis gasoline fraction can therefore be treated further in several steps. In this context, the selective hydration 21 of the entire pyrolysis gasoline fraction in order to convert acetylenes, dienes and styrenes to olefins is the most usual and is illustrated here. After the separation of higher molecular components (not illustrated), the correspondingly treated pyrolysis gasoline fraction can be supplied in the form of a substance flow k to a separation 22.

In the illustrated example, three fractions are formed in the separation 22 and removed in the form of corresponding substance flows. These are a fraction which contains predominantly or exclusively hydrocarbons with five carbon atoms (substance flow l), a fraction which contains predominantly or exclusively hydrocarbons with 6 to 8 carbon atoms (so-called heart cut, English: Heart Cut, substance flow m), and a fraction which contains predominantly or exclusively heavier hydrocarbons (substance flow n). The heart cut can be subjected to a hydro-desulphurisation 23, in which olefins are converted to paraffins and naphthenes, and organically bound sulphur is converted to hydrogen sulphide, which can be removed in a downstream stripper (not illustrated). The correspondingly treated heart cut is subjected in the form of a substance flow o to an aromatic extraction 24, in which aromatics (the already mentioned BTX fraction) are separated from aliphatics in a per se known manner. In the illustrated example, an aromatic flow p is output from the aromatic extraction 24; the aliphatics are not illustrated.

If required, the aromatic flow p is supplied together with the hydrogen flow g, designated here with q, compressed in a hydrogen compressor 31, to a conditioning 32, which can comprise, for example, a heating and optionally hydration, and is then supplied in the form of a feedstock flow r to a hydrodealkylation 33. A product mixture formed in the hydrodealkylation 33 is cooled (not shown) and supplied in the form of a product flow s to a phase separation 34. In the phase separation 34, a liquid fraction is separated, leaving a gaseous fraction. The gaseous fraction, which contains predominantly or exclusively the alkanes split off from the alkylated aromatics in the hydrodealkylation, the residual hydrogen and traces of aromatics, is removed in the form of a substance flow t. The liquid fraction, which contains predominantly aromatics, is transferred in the form of a substance flow u to a stabilisation 35, in which remaining residues of hydrogen and alkanes are removed. The removed fraction is drawn off in gaseous form as substance flow v.

There remains a liquid fraction which can be supplied in the form of a substance flow w, for example, to a clay treatment 26 (English: clay treatment) and then to a separation 37. In the separation 37, a fraction which contains predominantly or exclusively dealkylated aromatics, can be removed in the form of a substance flow x. Non-dealkylated aromatics can be recycled in the form of a substance flow y containing predominantly or exclusively such aromatics to the conditioning 32 or the hydrodealkylation 33. In the illustrated example, the substance flows t and v are combined in a combined flow z, which can be combined with the cracking-gas flow c upstream or in the compressor 15.

The invention claimed is:

1. A method for the manufacture of benzene comprising:
   a) forming a first feedstock mixture comprising alkylated aromatics and hydrogen;
   b) hydrodealkylating the first feedstock mixture to partially convert the alkylated aromatics with the hydrogen to benzene and obtain a first product mixture comprising benzene, unconverted alkylated aromatics, alkanes with one to three carbon atoms formed in the conversion of the alkylated aromatics to benzene, and unconverted hydrogen;
   c) separating at least a part of the alkanes with one to three carbon atoms and at least part of the hydrogen from the first product mixture to obtain a light-gas fraction;
   d) steam cracking a second feedstock mixture to form a steam cracking product mixture;
   e) subjecting the second product mixture to separation of a first pyrolysis gasoline fraction, sour gas removal, compression, drying and precooling steps;
   f) providing at least a part of the light-gas fraction and at least part of the steam cracking product mixture resulting from step e) to a cryogenic separation,
      wherein the cryogenic separation comprises forming a hydrogen fraction, a fraction predominantly or exclusively containing hydrocarbons with two carbon atoms, and a second pyrolysis gasoline fraction; and
      wherein the hydrogen fraction formed in the cryogenic separation comprises at least 75% by volume of hydrogen; and
   g) providing the hydrogen fraction to the first feedstock mixture as at least part of the hydrogen contained in the first feedstock mixture.

2. The method according to claim 1, wherein the at least a part of the light-gas fraction supplied to the cryogenic separation is compressed and then subjected to cryogenic separation.

3. The method according to claim 1, wherein the cryogenic separation comprises a demethanisation, and wherein the hydrogen contained in the first feedstock mixture is provided at least in part with the use of the demethanisation.

4. The method according to claim 1, wherein at least a part of the alkylated aromatics contained in the first feedstock mixture is provided through conditioning of at least a part of the first and/or second pyrolysis gasoline fraction.

5. The method according to claim 4, wherein the first feedstock mixture is poor in or free from non-aromatic hydrocarbons.

6. The method according to claim 4, wherein conditioning of the at least a part of the first and/or second pyrolysis gasoline fraction comprises a hydration, a separation, a hydro-desulphurisation, and/or an aromatic extraction.

7. The method according to claim 1, wherein the hydrogen provided by the cryogenic separation step and contained in the first feedstock mixture is subjected to a compression in order to form the first feedstock mixture.

8. The method according to claim 1, wherein the second feedstock comprises naphtha.

9. The method according to claim 1, wherein the alkylated aromatics comprise toluene and xylene.

10. The method according to claim 1, further comprising separating at least a part of the benzene and unconverted alkylated aromatics from the first product mixture to obtain a liquid fraction.

11. The method according to claim 10, further comprising separating at least a part of the liquid fraction to form a fraction containing predominantly or exclusively benzene and a fraction containing predominantly or exclusively the unconverted alkylated aromatics.

12. The method according to claim 11, further comprising recycling at least a part of the fraction containing predominantly or exclusively the unconverted alkylated aromatics to the hydrodealkylation.

\* \* \* \* \*